United States Patent [19]

Barberet et al.

[11] Patent Number: Plant 6,210

[45] Date of Patent: Jun. 21, 1988

[54] CARNATION NAMED LONWADEC

[75] Inventors: Nicole Barberet; Yves Ducloux, both of Antibes, France

[73] Assignee: Laboratoire de Physiologie Vegetale de la Londe, La Londe, France

[21] Appl. No.: 872,244

[22] Filed: Jun. 9, 1986

[51] Int. Cl.[4] ..... A01H 5/00

[52] U.S. Cl. ..... Plt./71

[58] Field of Search ..... Plt./71

*Primary Examiner*—James R. Feyrer

*Attorney, Agent, or Firm*—Charles W. Rummler; W. Dennis Drehkoff

[57] ABSTRACT

A new carnation plant particularly distinguished by its spray of relatively small, Venetian Pink blossoms which are borne in a cluster on a strong, upright stem having an average length of about 6.5 cm. and blooming recurrently with a profuse production of flowers in the spring, midseason and fall periods but having a tendency to give fewer blooms in the fall season. This plant has a vigorous, upright growth habit with an abundant foliage production and reaching an average height of about 98 cm. at eight months, the plant also being tolerant to *Fusarium oxysporum* as observed I.N.R.A., Antibes, France.

1 Drawing Sheet

BACKGROUND OF THE NEW PLANT

Our new spray carnation cultivar is the result of our breeding efforts carried on since 1983 at La Londe, Les Maures, France, with the object of producing plants of good quality having blooms of a nice, attractive color and particularly resistant to *Fusarium oxysporum*, this new plant originating as a seedling produced by our crossing of selected and individually identified plants from among our stock of plants maintained at La Londe for breeding purposes. This particular seedling was selected by us for propagation and test because of its delicate light pink flower color and its apparently favorable growth habit. This selected seedling was reproduced by us at La Londe by means of cuttings of the parent plant with very favorable results, which led us to direct further propagation at La Londe through several successive generations which established to our satisfaction that the novel and distinctive characteristics of the parent seedling were fully retained from generation to generation and appeared to be firmly fixed.

DESCRIPTION OF THE DRAWING

Our new spray carnation plant is illustrated by the accompanying photographic drawing which shows, in full color, a typical arrangement of flowers in various stages of opening, the colors shown being as nearly true to those specified herein as is reasonably possible to obtain by conventional photographic procedures.

DESCRIPTION OF THE NEW PLANT

The following is a detailed description of our new spray carnation plant based upon observations made at La Londe, Les Maures, France, the color designations being specified according to The R.H.S. Colour Chart published by The Royal Horticultural Society at London, England.

THE PLANT

Origin: Seedling.

Parentage:

*Seed parent.*—Stock Plant No. 79 MB 3.

*Pollen parent.*—Stock Plant No. 75 MR 10. These stock plants are unnamed and unpatented varieties maintained for breeding purposes in our collection of carnation plants at La Londe, France, and each of these plants is individually identified in our permanent breeding records.

Classification:

*Botanic.*—*Dianthus caryophyllus.*

*Commercial.*—Spray carnation.

Form: Tall, erect bush comprising at least four stems emitted near the ground from a main stem having a length of about 15 cm. due to pinching.

Height (at 8 months): Averaging about 98 cm.

Growth habit: Vigorous, upright and rather rigid.

Foliage:

*Quantity.*—Abundant.

*Number of leaves.*—More than 120.

*Leaf size (at the 7th node).*—About 12.5 cm. long and about 1.1 cm. wide, in average.

*Shape.*—Linear with curved margins and acuminate tips.

*Texture.*—Leathery.

*Color.*—Both upper and lower sides, 189A.

*Ribs, veins and rachis.*—Barely noticeable.

THE BUD

Form: Ovoid.

Size:

*Diameter.*—Averaging about 1.4 cm.

*Length.*—Averaging about 2.4 cm.

Rate of opening: Normal for carnations.

Color of petals:

*When sepals first divide.*—49D.

*When petals begin to unfurl.*—49C.

Sepals:

*Shape.*—The sepals are joined at the lower part and the upper part is of ovate character with sharp pointed apex.

*Number.*—Five. The sepals are hooded over the bud and when the flowers open the sepals stand up.

*Color.*—Inside — 145D. Outside — 139C and 144C.

*Striae.*—The striae are longitudinal.

Calyx:

*Shape.*—Long cylindrical.

*Splitting.*—The calyx does not split.
*Aspect.*—Smooth.
Flower stem:
*Length.*—About 65 cm. (in average).
*Character.*—Erect and rather rigid.
*Color.*—189A.

THE FLOWER

Blooming habit: Recurrent and profuse during spring, midseason and fall with a tendency to give fewer blooms in fall.
Size of bloom: Small.
*Diameter.*—Averaging about 5.3 cm.
*Depth.*—Averaging about 4.2 cm.
Borne: In a cluster.
Shape:
*When bloom first opens.*—High centered.
*When bloom matures.*—Dome shaped.
Petalage:
*Number of petals.*—Averaging about 53.
*Arrangement.*—Imbricated.
*Form.*—The petals are fan-shaped with rounded edges and serrated apex.
*Texture.*—Leathery.
*Appearance.*—Satiny.
*Color.*—Outer petals, 49C with greenish base. Reverse side, 49D. Inside petals, 49C with greenish base. Reverse side, 49D.
Petaloids:
*Number.*—Usually less than 12.
*Size.*—Smaller than the petals.
*Color.*—The same as the petals.
Flower stem:
*Length.*—Cut at tenth node, the length averages about 65 cm.
*Character.*—Upright with good strength.
*Color.*—189A.
Fragrance: Strong
Persistence: The flowers hang on and dry.
Lasting quality: At least ten days in vase keeping.
Disease resistance: Tolerant to *Fusarium oxysporum* as observed I.N.R.A., Antibes, France.

REPRODUCTIVE ORGANS

Stamens:
*Number.*—3 to 12 arranged around the ovary.
Anthers:
*Size.*—About 4 mm.
*Color.*—Whitish.
Filaments:
*Length.*—About 2.8 cm., in average.
*Color.*—Whitish.
Pistils:
*Number.*—Two.
Styles:
*Length.*—About 2.2 cm., in average.
*Color.*—White.
Stigmas:
*Color.*—Whitish.
Character of ovaries: Lightly ribbed.

This new spray carnation most nearly resembles "Londaison" (U.S. Plant Pat. No. 5,789) but differs materially by having a more uniform color, somewhat less vegetation, and being tolerant to *Fusarium oxysporum.*

We claim:

1. A new and distinct spray carnation cultivar, substantially as herein shown and described, characterized by the very light pink uniform coloration of its relatively small blooms, the production of which is abundant during its blooming seasons.

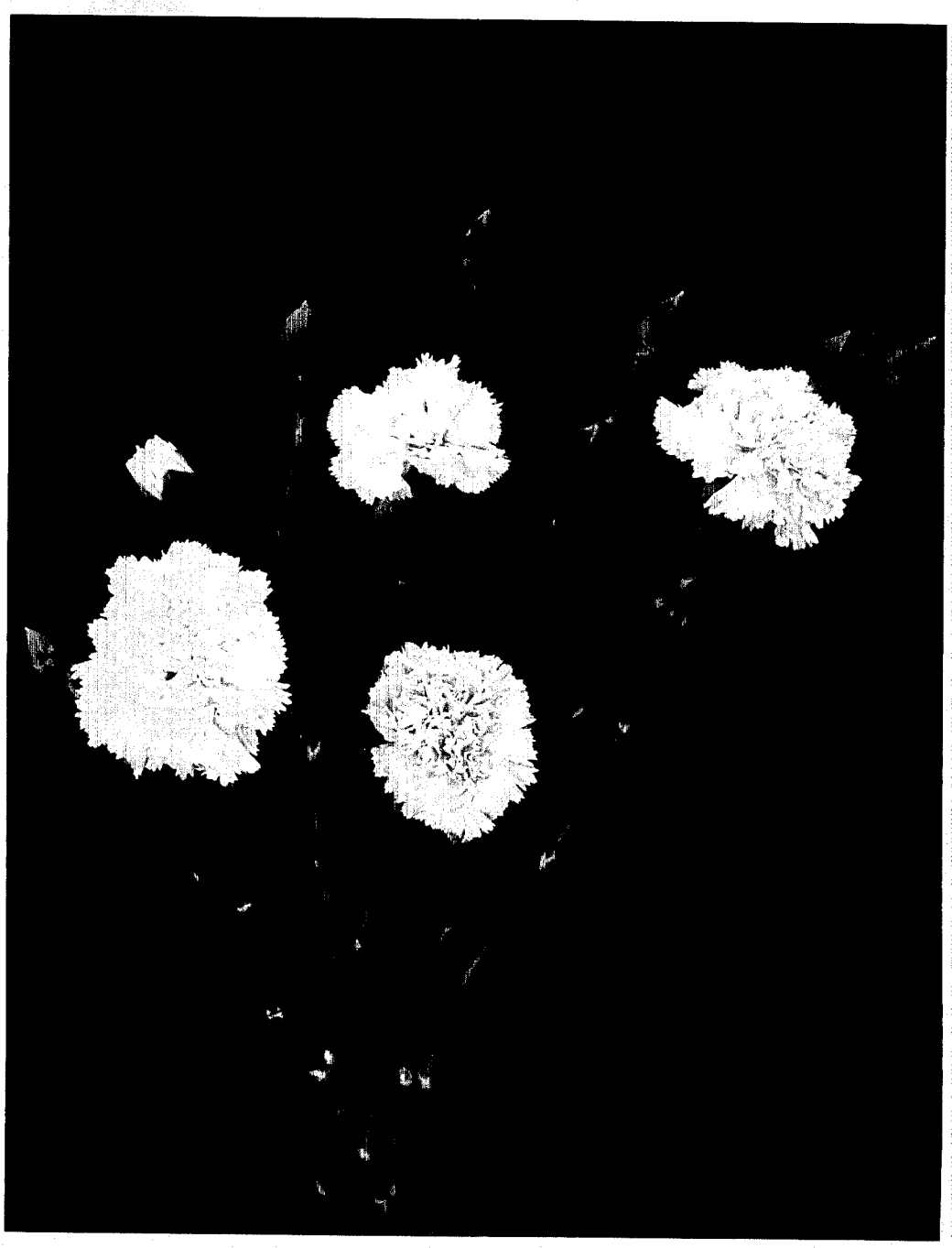

* * * * *